(12) United States Patent
Goldfarb et al.

(10) Patent No.: US 9,750,620 B2
(45) Date of Patent: Sep. 5, 2017

(54) SYSTEMS AND CONTROL METHODOLOGIES FOR IMPROVING STABILITY IN POWERED LOWER LIMB DEVICES

(75) Inventors: Michael Goldfarb, Franklin, TN (US); Huseyin Atakan Varol, Astana (KZ); Brian Edward Lawson, Nashville, TN (US); Frank Charles Sup, Amherst, MA (US)

(73) Assignee: VANDERBILT UNIVERSITY, Nashville, TN (US)

( * ) Notice: Subject to any disclaimer, the term of this patent is extended or adjusted under 35 U.S.C. 154(b) by 939 days.

(21) Appl. No.: 13/508,175

(22) PCT Filed: Oct. 29, 2010

(86) PCT No.: PCT/US2010/054655
§ 371 (c)(1),
(2), (4) Date: May 4, 2012

(87) PCT Pub. No.: WO2011/096965
PCT Pub. Date: Aug. 11, 2011

(65) Prior Publication Data
US 2012/0221119 A1    Aug. 30, 2012

Related U.S. Application Data

(60) Provisional application No. 61/258,079, filed on Nov. 4, 2009.

(51) Int. Cl.
*A61F 2/68*    (2006.01)
*A61F 2/64*    (2006.01)
(Continued)

(52) U.S. Cl.
CPC .................. *A61F 2/68* (2013.01); *A61F 2/60* (2013.01); *A61F 2/64* (2013.01); *A61F 2/6607* (2013.01);
(Continued)

(58) Field of Classification Search
CPC ...... A61F 2/48; A61F 2/64; A61F 2/66; A61F 2/68; A61F 2/70; A61F 2002/6818; A61F 2002/701
(Continued)

(56) References Cited

U.S. PATENT DOCUMENTS

| 6,755,870 B1 | 6/2004 | Biedermann et al. |
| 2009/0030530 A1 | 1/2009 | Martin |

FOREIGN PATENT DOCUMENTS

WO    2007/027808    3/2007

OTHER PUBLICATIONS

International Search Report for International Application No. PCT/US2010/054655, International Filing Date: Oct. 29, 2010.
(Continued)

*Primary Examiner* — Bruce E Snow
(74) *Attorney, Agent, or Firm* — Nixon Peabody LLP; Eduardo J. Quinones

(57) ABSTRACT

Systems and methods are provided for controlling a lower limb device having at least one powered joint. The method includes detecting a stumble event based on one or more sensor signals associated with an overall motion lower limb device, classifying the stumble event based on sensor signals following the sensor signals associated with the stumble event, and selecting a stumble recovery strategy for the lower limb device based on the classification of the stumble event.

10 Claims, 11 Drawing Sheets

(51) Int. Cl.
*A61F 2/60* (2006.01)
*A61F 2/66* (2006.01)
A61F 2/50 (2006.01)
A61F 2/70 (2006.01)
A61F 2/76 (2006.01)

(52) U.S. Cl.
CPC . *A61F 2002/5033* (2013.01); *A61F 2002/607* (2013.01); *A61F 2002/701* (2013.01); *A61F 2002/704* (2013.01); *A61F 2002/764* (2013.01); *A61F 2002/7635* (2013.01)

(58) Field of Classification Search
USPC .................................. 623/24, 43–45, 50–52
See application file for complete search history.

(56) References Cited

OTHER PUBLICATIONS

Written Opinion, for International Application No. PCT/US2010/054655, International Filing Date: Oct. 29, 2010.

Aeyels, et al., "An EMG-based finite state approach for a microcomputer-controlled above-knee prosthesis", Engineering in Medicine and Biology Society, IEEE 17th Annual Conference Montreal, Que., Canada, vol. 2, Sep. 20, 1995, pp. 1315-1316.

Forner, Cordero, "Multiple-Step Strategies to Recover From Stumbling Perturbations", Gait & Posture, vol. 18, No. 1, Aug. 1, 2003, pp. 47-59.

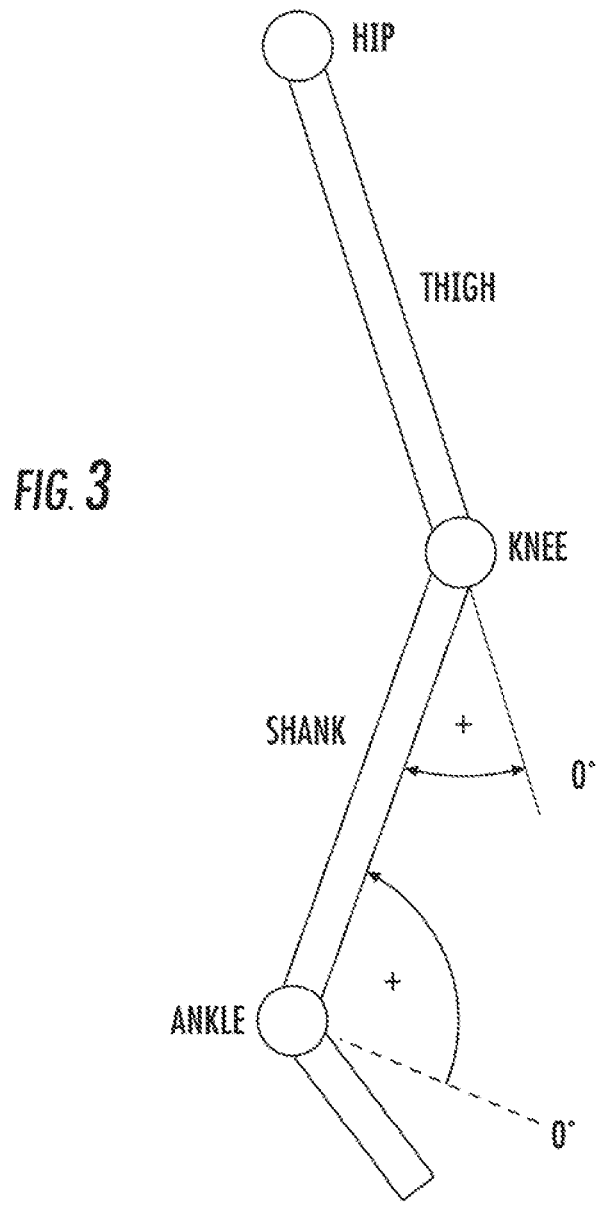

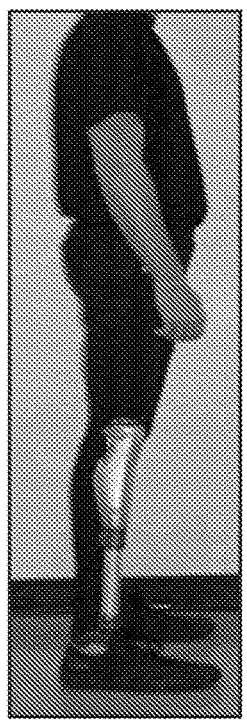  
FIG. 9A  FIG. 9B  FIG. 9C
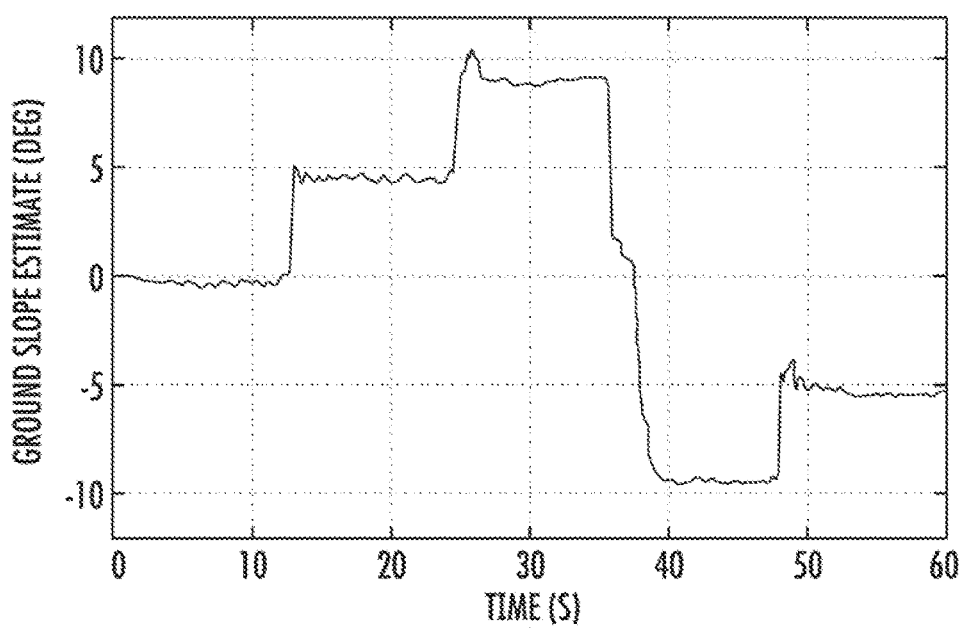
FIG. 10

SYSTEMS AND CONTROL METHODOLOGIES FOR IMPROVING STABILITY IN POWERED LOWER LIMB DEVICES

CROSS-REFERENCE TO RELATED APPLICATIONS

This application is a §371 national stage entry of International Application No. PCT/US2010/054655, filed Oct. 29, 2010, which claims priority to U.S. Provisional Application No. 61/258,079, filed Nov. 4, 2009 both of which are hereby incorporated by reference.

FIELD OF THE INVENTION

The invention relates to powered lower limb devices and control systems and methodologies for controlling the powered lower limb devices to improve stability during standing or walking.

BACKGROUND

Leg prostheses can provide an artificial ankle, and artificial knee, or both an artificial ankle and an artificial knee. A transfemoral prosthesis is a prosthesis designed for above the knee amputees. Transfemoral prostheses are generally more complicated than transtibial prostheses, as they must include a knee joint. Such leg prostheses have been used successfully to restore mobility and freedom of many lower leg amputees. However, various issues still plague existing leg prostheses. One significant issue with existing leg prostheses is falls and far of falling among lower limb amputees. Approximately one in five lower limb amputees have reported sustaining an injury as a result of a fall within the last year, with about half of these lower limb amputees reporting that they have required medical attention.

Lower limb amputee falls are typically the result of the inability of state-of-the-art passive prostheses to provide proper joint kinetics and kinematics (particularly in conditions of uneven terrain). These limitations can severely compromise the standing and walking stability of the lower limb amputee (particularly of the transfemoral amputee), and thus increase the likelihood of a stumble or fall. Further, in the case of stumbling, these prostheses largely lack the ability to appropriately react (i.e., provide a recovery response), thus significantly increasing the likelihood that a stumble will result in a fall.

SUMMARY

Embodiments of the invention provide systems and methods for controlling powered lower limb devices to improve stability during standing or walking. In a first embodiment of the invention, a method of controlling a lower limb device, having at least a powered joint is provided. The method includes the step of detecting a stumble event based on one or more sensor signals associated with the motion of the lower limb device. The method also includes the step of classifying the stumble event based the sensor signals following the stumble event. The method further includes the step of selecting a stumble recovery strategy for the lower limb device based on the classification of the stumble event.

In a second embodiment of the invention, a control system for a lower limb device having at least one powered joint is provided. The control system includes a plurality of sensors for generating one or more sensor signals associated with at least an overall motion of the lower limb device. The control system further includes at least one processor coupled to the plurality of sensors and for generating one or more control signals for the lower limb device. Additionally, the control system also includes a first module for causing the processor to detect a stumble event based on the sensor signals and a second module for causing the processor to classify the stumble event based on a second portion of the sensor signals following a first portion of the sensor signals associated with the stumble event. Further, the control system also includes a third module for causing the processor to select a stumble recovery strategy for the lower limb device based on the classification of the stumble event and a fourth module for causing the processor to generate the control signals according to the selected stumble recovery strategy.

In a third embodiment of the invention, a method of controlling a lower limb device coupled to a thigh and having at least a leg portion, a foot portion, a powered knee joint, and a powered ankle joint is provided. The method includes detecting an initial contact of the foot portion with a walking surface based on a plurality of load sensors disposed along a length of the plantar surface of the foot portion. The method further includes lowering an impedance of the ankle joint until contact of a substantial portion of the plantar surface and the walking surface is detected based on the plurality of load sensors. Additionally, the method includes computing a slope of the walking surface based on a plurality of sensors disposed in the foot portion or the leg portion, and configuring the ankle joint to provide dorsiflexion or plantarflexion of the foot with respect to an equilibrium configuration for the foot and restoring the impedance of the ankle joint until separation of the foot from the walking surface, wherein an amount of dorsiflexion or plantarflexion is based on the computed slope.

BRIEF DESCRIPTION OF THE DRAWINGS

FIG. 3 shows the joint angle and torque convention used herein. Positive torque is defined in the direction of increasing angle.

FIGS. 9A-9C depicts a transfemoral amputee subject, wearing a state-of-the-art passive prosthesis (i.e., an Otto Bock C-leg with a Freedom Renegade ankle/foot), for various slopes.

FIG. 10 shows real-time ground slope estimation obtained from a transfemoral amputee standing on various ramps of various slopes (+5, +10, −10, and −5).

DETAILED DESCRIPTION

Figure 1A:
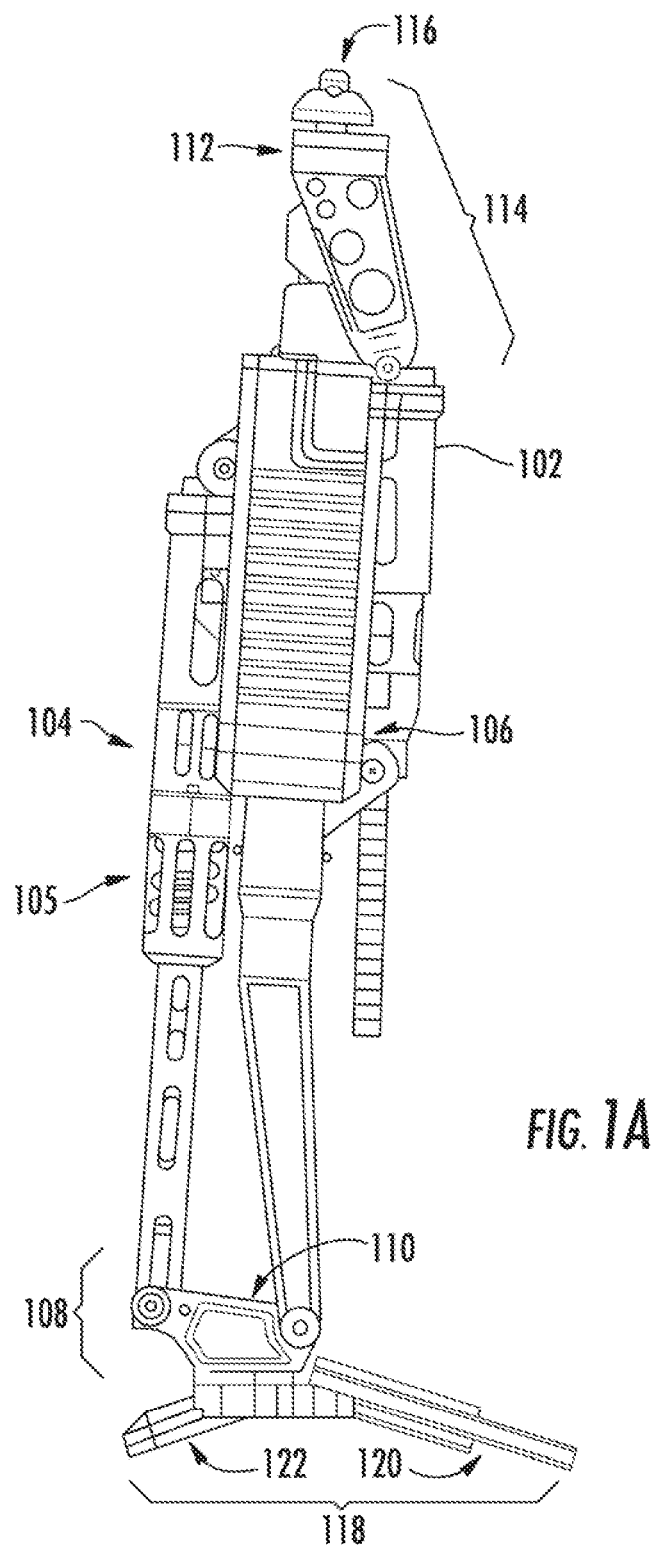
FIG. 1A is a side view of powered knee and ankle prosthesis, according to another embodiment of the invention.

The invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a fill understanding of the invention. One having ordinary skill in the relevant art, however, will readily recognize that the invention can be practiced without one or more of the specific details or with other methods. In other instances, well-known structures or operations are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

The present invention applies to lower limb devices, such as prostheses and orthoses (or exoskeletons) with at least one powered joint, for which the physical behavior of the joint can be electronically controlled. The present inventors have observed that recent advances in robotics technology have enabled the development of powered lower limb prostheses, which have the capability of offering biomechanically useful levels of joint torque and power. Along with effective intent recognition and control, such powered transfemoral and transtibial prostheses can provide enhanced mobility relative to state-of-the-art passive prostheses. As used herein, the term "passive prosthesis" refers to any prosthesis without the ability to deliver net mechanical power output at the joints. In addition to enhancements in mobility, powered prosthesis additionally have the capability to provide active stumble recovery behaviors, in addition to actively and reflexively adapting to various perturbations in ground topography (e.g., uneven ground) and disturbances in standing stability (e.g., from being pushed unexpectedly), and therefore have the potential to actively enhance recovery from imbalance and thus reduce the number of fails of lower limb amputees.

Accordingly, the various embodiments of the invention provide a control system and methodology for providing stumble recovery and balance enhancement behaviors for enhanced standing and walking stability in lower limb devices with at least one powered joint. In particular, the various embodiments of the invention provide a new control methodology for lower limb devices, such as prosthetic device, orthotic device, or robotic devices, for implementing improved balance control and for detecting and responding to stumble events. In the various embodiments of the invention, this control methodology can be combined with or within an existing powered lower limb device control system that restores mobility and provides greater stability for lower limb amputees as compared to conventional passive lower limb prostheses.

Although the various embodiments of the invention will be generally described with respect to prosthetic devices with powered knee and/or ankle joints, this is solely for ease of illustration. As described above, the control systems and methodologies described herein are equally applicable for use with any type of lower limb device, including prosthetic, orthotic, and robotic devices. Further, the control systems and methodologies are equally applicable to any other devices including other types of joints.

Figure 1B:
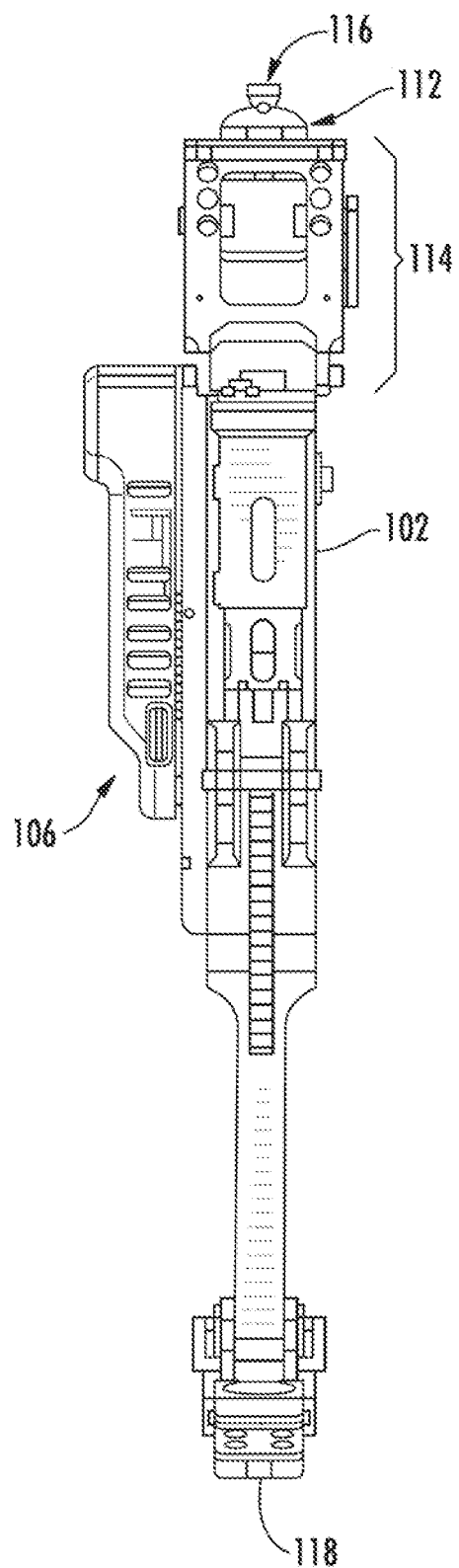
FIG. 1B is a front view of powered knee and ankle prosthesis of FIG. 1A.
Figure 2A:
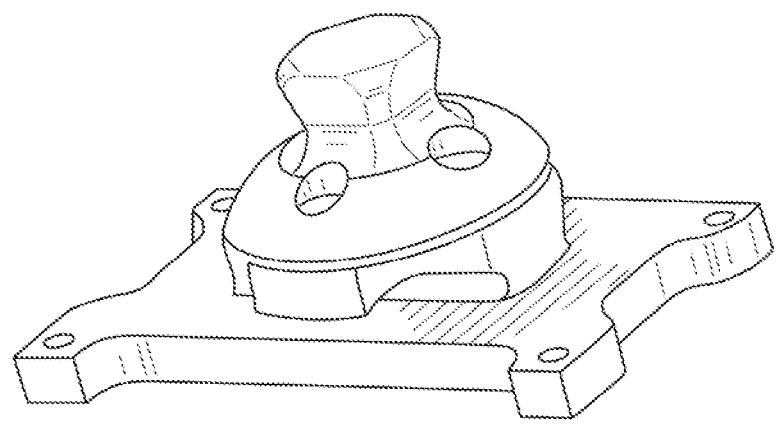
FIGS. 2A and 2B show perspective and bottom views of an exemplary sagittal moment load cell suitable for use in the various embodiments of the invention.
Figure 2B:
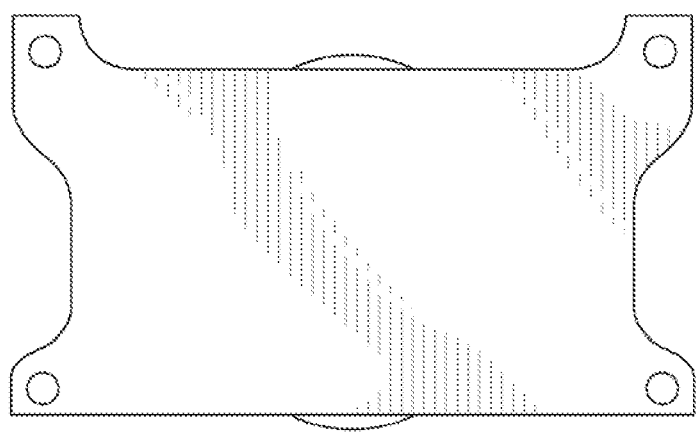

One design for a prosthesis that can be operated according to an embodiment of the invention is shown in FIGS. 1A and 1B. FIG. 1A is a side view of powered knee and ankle prosthesis 100, according to another embodiment of the invention. FIG. 1B is a front view of powered knee and ankle prosthesis of FIG. 1A. FIGS. 2A and 2B show perspective and bottom views of an exemplary sagittal moment load cell suitable for use in the various embodiments of the invention.

Each joint actuation unit, such as knee actuation unit 102 and ankle actuation unit 104 in 1A, can include a uniaxial load cell positioned in series with the actuation unit for closed loop force control. Both the knee and ankle joints can incorporate integrated potentiometers for joint angle position. The ankle actuation unit can include a spring 105, as described above with respect to FIGS. 1A-4. One 3-axis accelerometer can be located on the embedded system 106 and a second one can located below the ankle joint 108 on the ankle pivot member 110. A strain based sagittal plane moment sensor 112, such as sensor 200 shown in FIGS. 2A and 2B, can located between the knee joint 114 and the socket connector 116, which measures the moment between a socket and the prosthesis. In the various embodiments of the invention, a sagittal plane moment sensor can be designed to have a low profile in order to accommodate longer residual limbs. The sensor can incorporate a full bridge of semiconductor strain gages which measure the strains generated by the sagittal plane moment. In one embodiment of the invention, the sagittal plane moment sensor was calibrated for a measurement range of 100 Nm. A custom foot 118 can be designed to measure the ground reaction force components at the ball 120 of the foot and heel 122. The foot can include heel and ball of foot beams, rigidly attached to a central fixture and arranged as cantilever beams with an arch that allows for the load to be localized at the heel and ball of the foot, respectively. Each heel and ball of foot beam can also incorporate a full bridge of semiconductor strain gages that measure the strains resulting from the respective ground contact forces. In one embodiment of the invention, the heel and ball of foot load sensors were calibrated for a measurement range of 1000 N. In addition, incorporating the ground reaction load cell into the structure of a custom foot can eliminate the added weight of a separate load cell, and also enable separate measurement of the heel and ball of foot load. The prosthetic foot can be designed to be housed in a soft prosthetic foot shell (not shown).

Although FIGS. 1A and 1B show a transfemoral prosthesis with a powered knee joint and ankle joint, other embodiments could include a transfemoral prosthesis with a powered knee joint and passive ankle joint, a transfemoral prosthesis with a passive knee joint and powered ankle joint, or a transtibial prosthesis with a powered ankle joint.

As described above, the control systems and methodologies according to the various embodiments of the invention can be combined with existing control systems for lower limb devices. For example, the various embodiments of the invention can be used to enhance existing control frameworks for generating the required joint torques for locomotion while ensuring stable and coordinated interaction with the user and the environment. This enables embodiments of the invention to restore substantially biomechanically normal locomotion and provide a sufficient amount of stability during standing and walking to prevent many types of falls.

Prior to describing the various embodiments of the invention in detail, it may be useful to describe operation of a lower limb control system in order to more fully understanding how the control methodology of the present invention can be combined with an existing control system. This will described in relation to FIG. 3. FIG. 3 shows the joint angle and torque convention used herein. Positive torque is defined in the direction of increasing angle.

In general, the torque required at each joint of a lower limb device during a single stride (i.e., a single period of gait) can be piecewise represented by a series of impedance functions. A regression analysis of gait data indicates that joint torques can be characterized by functions of joint angle ($\theta$) and angular velocity by an impedance model, such as the following exemplary impedance function shown in equation 1 below:

$$\tau = k_1(\theta - \theta_e) + b*\dot{\theta} \quad (1)$$

where the impedance consists of a stiffness $k_1$, a damping coefficient b, and the equilibrium joint angle $\theta_e$. These parameters are typically constants (although they need not be constant), and are generally generated empirically for a given joint during a given internal phase (e.g., knee, internal Phase 3). $k_1$ characterizes the linear stiffness. b is the linear damping coefficient, $\theta$ is the measured joint angle which can characterize the state of the prosthesis, $\theta_e$ is the equilibrium angle, $\dot{\theta}$ is the angular velocity of the joint, and $\tau$ is the joint torque. Given these parameters, together with instantaneous sensor measurements for $\theta$ and $\dot{\theta}$, the torque ($\tau$) at the joints (knee and ankle) can be determined. Positive directions of the angle ($\theta$) and torque ($\tau$) as used herein are defined as shown in FIG. 3.

Figure 4:
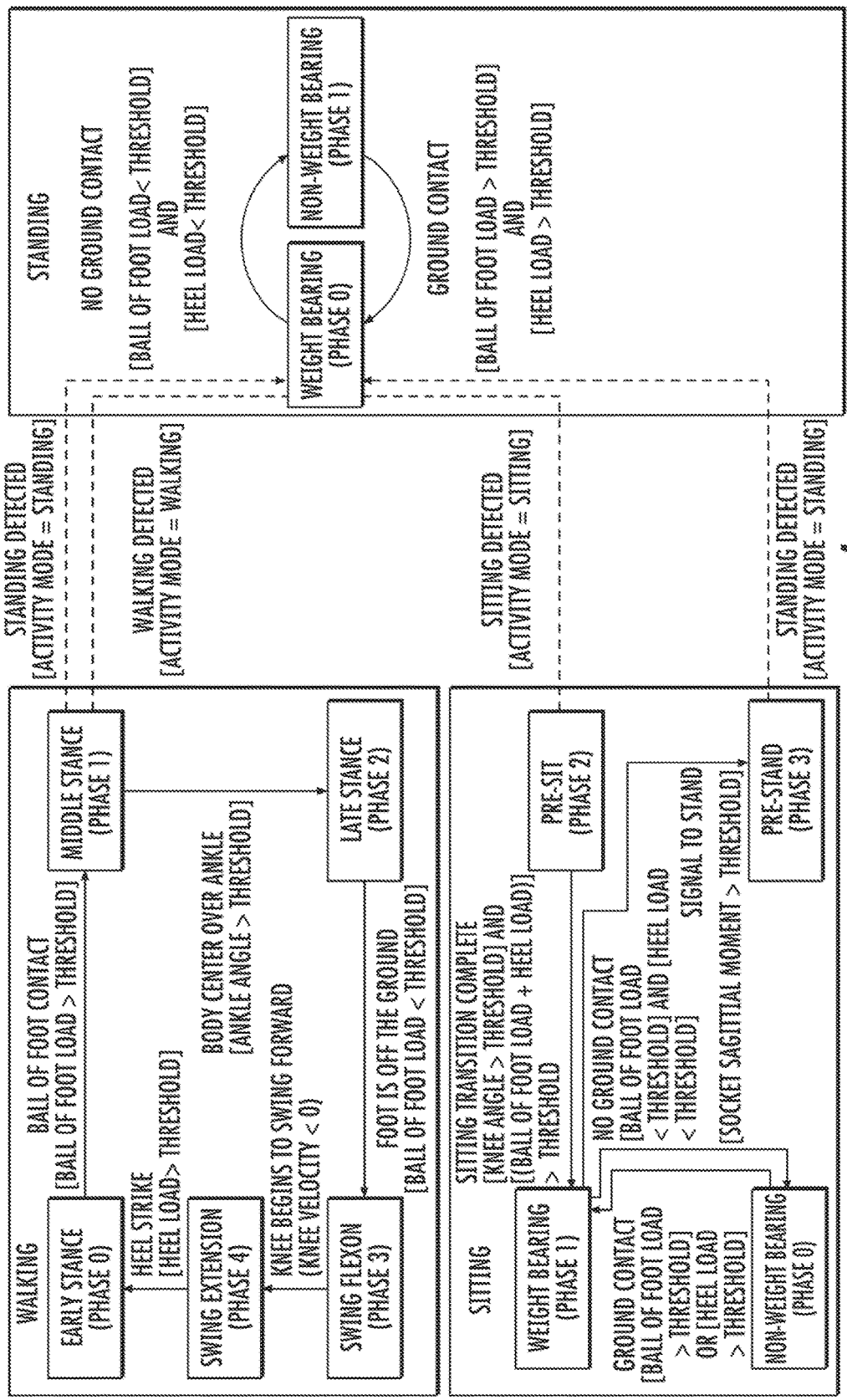
FIG. 4 is a control state chart for the three activity modes corresponding to walking, standing, and sitting, and for the internal phases and their corresponding transitions within each activity mode.

As described above, the decomposition of joint behavior into segments requires the division of the gait cycle into a plurality of internal phases or "finite states" characterized by an impedance function and a set of constants for the impedance function, as dictated by their functions and the character of the piecewise segments of the impedance functions described above. The switching rules between internal phases should generally be well defined and measurable, and the number of phases should be sufficient to provide a substantially accurate representation of normal joint function. Thus, the swing and stance phase of gait can constitute a minimal set of internal phases, as shown in FIG. 4. FIG. 4 (upper left-hand box) shows exemplary switching rules during the walking cycle for 5 discrete phases. As indicated in FIG. 4, switching between phases can be based on the ankle angle >a threshold value (walking Phase 1 to walking Phase 2), or ball of foot load (i.e., ankle torque)<threshold (walking Phase 2 to walking Phase 3), the angle or torque measurements provided by on board sensors as described above.

Phase 0 begins after a heel strike by the user (which can be sensed by the heel sensor), upon which the knee immediately begins to flex so as to provide impact absorption and begin loading, while the ankle simultaneously plantarflexes to reach a flat foot state. Both knee and ankle joints have relatively high stiffness (and can be accounted for by k1 in equation 1) during this phase to prevent buckling yet allow for appropriate stance knee flexion, because Phase 1 comprises most of the weight bearing functionality. Phase 2 is the push-off phase and begins as the ankle dorsiflexes beyond a given angle (i.e., the user's center of mass lies forward of stance foot). The knee stiffness decreases in this mode to allow knee flexion while the ankle provides a plantarflexive torque for push-off. Phase 3 begins as the foot leaves the ground as detected by the ankle torque load cell and lasts until the knee reaches maximum flexion. Phase 4 is active during the extension of the knee joint (i.e., as the lower leg swings forward), which begins as the knee velocity becomes negative and ends at Phase 0 with a heel strike (e.g., as determined by the heel force sensor). In both of the swing phases (Phases 3 and 4), the ankle torque can be small and can be represented in the controller as a (relatively) weak spring regulated to a neutral position. The knee can be primarily treated as a damper in both swing phases.

Additional controls can be provided for operating the prosthesis when going from a sitting to a standing position or vice versa, as shown in FIG. 4 (lower-left hand box and right hand box).

The control system described above, and others that provide similar functionality, can be supplemented with stumble recovery and ground adaptation behaviors. In healthy biomechanics, recovery responses provide important mechanisms to aid in balance recovery during walking.

Tripping over an obstacle is recognized as one of the most common causes of falling. Such tripping typically induces one of two active responses in a human. When the perturbation occurs in early swing, humans typically demonstrate an elevating strategy, which consists of two distinct motion objectives, characterized by two distinct periods of motion. In the first period of motion, the hip, knee, and ankle joints exhibit active flexion, which effectively elevates the foot above the obstacle, while also carrying the foot forward in space. In the second period of motion, the hip continues to flex, while the knee and ankle joints actively extend, which effectively accelerates the foot forward and toward the ground. This can alternatively be interpreted as arresting the forward angular momentum imparted to the body by impact with the obstacle. Note that due to collision with the obstacle, the foot is decelerated significantly while the forward momentum of the body center of mass is relatively unaffected. Maintaining stability of the walking limit cycle generally requires that the foot be located forward of the body COM at heel strike. The effect of the elevating strategy is thus to clear the obstacle and place the swing foot at a point (in the sagittal plane) that will arrest the forward angular momentum of the body.

When the swing leg experiences a perturbation late the swing phase, subjects generally demonstrate a lowering strategy. This case essentially amounts to a premature heel (or in this case foot) strike, induced by collision with the obstacle. As such, the swing leg knee joint extends and stiffens in a manner consistent with early stance phase, which initiates an early triggering of swing phase in the contralateral limb. In general, the limb that steps forward to arrest forward angular momentum of the body is referred to as the "recovery limb." Using this terminology, the swing leg serves as the recovery limb during the elevating strategy, while the stance leg serves as the recovery limb during the lowering strategy. Thus, tripping over an obstacle in the absence of such stumble recovery mechanisms will lead to a fall. In particular, since stumble recovery responses are active responses, thus requiring power from the joints, these recovery mechanisms cannot be reproduced by passive prostheses. The lack of such recovery responses is a likely contributor to the increased incidence of falls in the lower limb amputee population.

In the various embodiments of the invention, the stumble recovery process begins with detection of a stumble event. In particular, a stumble event is detected via monitoring of the overall acceleration of the leg. This can be done, for example, by measuring the acceleration of the thigh, shank, and/or foot during the swing phase of gait. Relative to such acceleration measurements, a stumble is a high-frequency event which can be quickly detected by assessing the magnitude of the acceleration and/or the power spectrum of the sagittal plane acceleration of the respective leg segments. This is illustrated in FIGS. 5A and 5B.

Figure 5A:
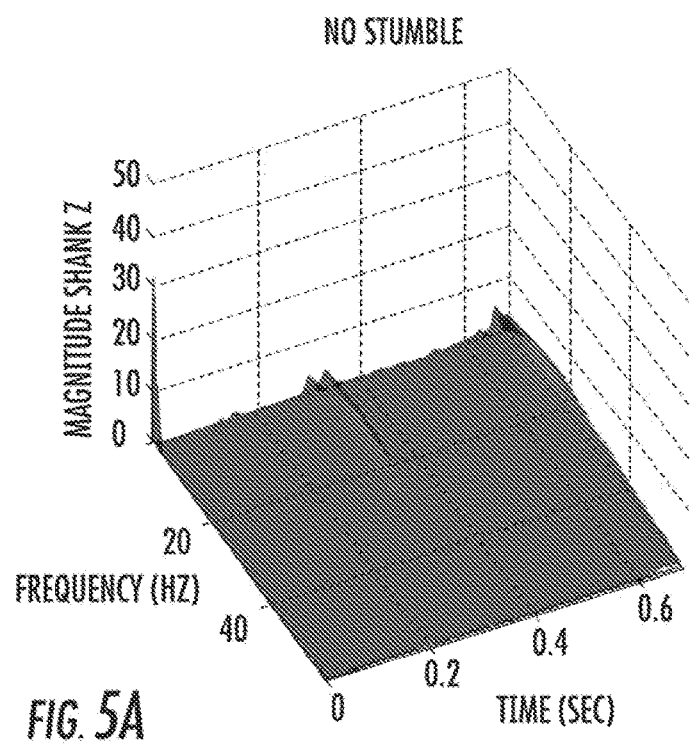
FIGS. 5A and 5B show the power spectrum versus time for a sagittal plane component of a shank acceleration during a typical (non-stumble) swing phase and for a swing phase in which a stumble event occurred, respectively.
Figure 5B:
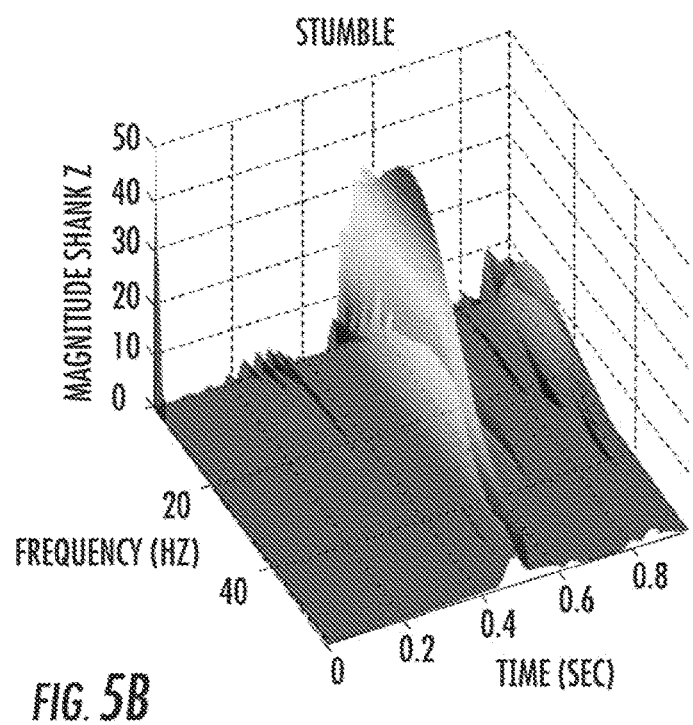

FIGS. 5A and 5B show an exemplary power spectrum versus time for a sagittal plane component of a shank acceleration during a typical (non-stumble) swing phase and for a swing phase in which a stumble event occurred, respectively. For purposes of FIGS. 5A and 5B, a 64-sample fast Fourier transform (FFT) using a Hamming window is computed at each one millisecond sampling interval in order to minimize the detection delay. Further, in order to enhance the robustness of this detection approach, the FFT was computed for the two sagittal plane acceleration components for each of the three leg segments, and a stumble was determined to occur when the FFT of at least four channels exceeded a predetermined threshold in magnitude in a given 100 msec interval. This algorithm was tested for a set of datasets, which included 19 stumbles and 33 control strides from 10 subjects. The algorithm correctly detected stumble (and absence of stumble) in all datasets, with an average delay of detection of 50 msec, and a maximum delay of detection of 70 msec. It is worth noting that the delay in the stumble response in healthy subjects is typically more than 100 msec. Accordingly, the delay required by the FFT approach described above will be well within the reaction time of healthy subjects.

It is worth noting that the FFT approach described herein is not a pattern classifier, and thus need not be trained. Further, unlike generation of a database for the training of various activity modes (e.g., walking and sitting), generating a database of stumbles for a classifier (in a commercial product) would be neither safe nor practical. Thus, the generalized approach described herein is more robust than pattern classification methods, as it does not require training and is applicable to all stumble circumstances.

After a stumble event is detected, the event may then be classified as either a lowering or elevating event. In particular, the recovery behavior in response to the stumble can be determined. That is, the response above the powered joint or the overall motion of the lower limb device can be determined in order to ascertained how to adjust the powered joints during the response. This determination can be made by monitoring the acceleration or motion of one or more portions of the lower limb following the stumble event. For example, in some embodiments, the acceleration or motion of the thigh portion of the lower limb can be directly measured. In another embodiment, the signals from sensors in the knee, shank, ankle, and/or foot portions of the prosthesis can be used to infer or estimate the acceleration or motion of the thigh portion. Regardless of the type of measurement, the measurements can be used to extract the type of motion being used to recover from the stumble.

Figure 6:
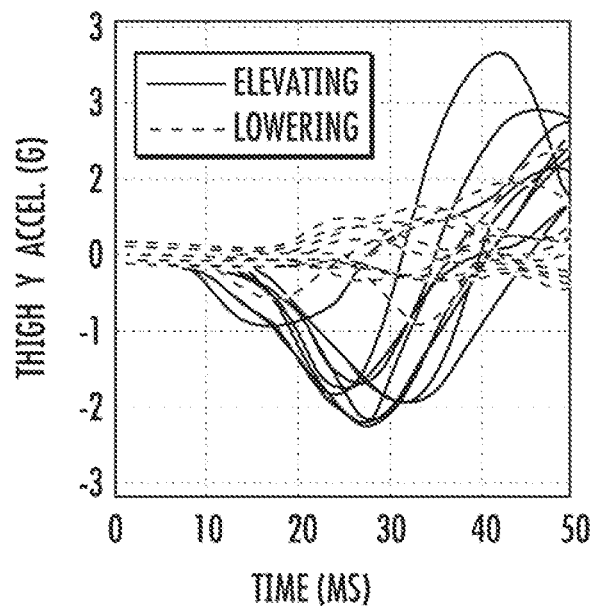
FIG. 6 shows the y-direction (i.e., transverse) component of the thigh segment acceleration for the 50 msec following various stumble events.
Figure 7:
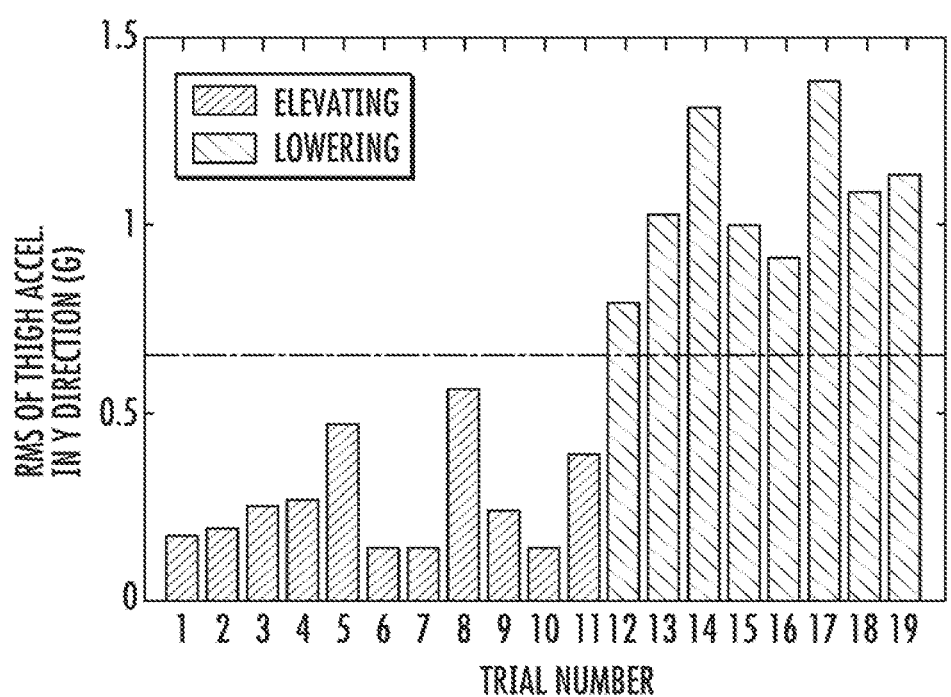
FIG. 7 shows that the root-mean-square of y-direction component of acceleration for the 50 msec following the various stumble events of FIG. 6.

FIG. 6 shows the y-direction (i.e., transverse) component of the thigh segment acceleration for the 50 msec following a stumble event for various subjects, where the dark traces are the cases in which the subjects employed an elevating strategy, and the light traces on the cases in which the subjects employed a lowering strategy. As can be observed from the figure, the character of the acceleration is distinct between the elevating and lowering responses. Thus this difference can be exploited for purposes of classification. For example, FIG. 7 shows that the root-mean-square of this component of acceleration for the 50 msec following the stumble event for the stumbles shown in FIG. 6. As can be seen from FIG. 7, a criteria consisting of a simple threshold of this acceleration measurement can be used to determine the stumble strategy for various stumbles.

The various embodiments are not limited to the exemplary methods of FIGS. 6 and 7. Rather, any other techniques for distinguishing between types of responses can be used in the various embodiments of the invention without limitation.

For example, in some embodiments of the invention, the type of event can be estimated from a state of the lower limb device. That is, the most likely of an elevating or a lowering strategy can be estimated based on when the stumble event occurs during a swing. In particular, near the beginning or the end of the swing, a lowering strategy is common among many users. In between, an elevating strategy is common among these same users. Accordingly, in one configuration, the sensors in the lower limb device can be used to detect a percentage of the swing that has been completed. Thereafter, the signals from these sensors can be compared to criteria in order to estimate the most likely recover strategy of the user. In another configuration, the angle of one or more joints can be used to determine the state of the lower limb device. Therefore, since the lower limb device will have different angles depending on the position of the swing, the control system can use the state of the lower limb device to estimate position in the swing and the most likely recovery strategy of the user.

Additionally, percentage of swing or joint angle information can be used in other ways. For example, this information can be used to verify the selection of an elevating or lowering response. In another example, a user may employ several different types of elevation or lowering strategies when a stumble occurs. That is, when an elevating strategy is used in response to a stumble near the beginning of the swing and near the end of the swing, different configurations of the lower limb device can be used to further mitigate the occurrences of falls. Similarly different configurations of the lower limb device can also be used in response to a lower strategy. Thus, different sub-classifications of lowering events and elevating events can be provided in the various embodiments of the invention and appropriate recovery strategies can be provided for each sub-classification. These sub-classifications can be identified in various ways. For example, in some configurations, the sub-classification can be based on a percentage of the swing that was completed prior to the occurrence of the stumble event. Thus for particular percentages, particular sub-classifications can be selected and the appropriate stumble recovery strategy for the lower limb device can be used. In other configurations, the sub-classification can also be based on a configuration of one or more joints at the time the stumble event occurs, such as the knee or ankle joint. Thus for particular angles of the joint, particular sub-classifications can be selected and the appropriate stumble recovery strategy for the lower limb device can be used.

Additionally, although the various embodiments are described herein with respect to monitoring acceleration, the invention is not limited in this regard. Rather, a combination of motion vectors, such as displacement, velocity, and acceleration can be used to detect stumble events and determine the type of stumble event, and force and torque measurements on the leg or foot can also be used to infer the appropriate response.

Once the appropriate stumble strategy of the user is identified, a stumble response controller is required to provide the appropriate response. If heel and/or ball of foot load sensors detect the onset of load bearing or sensors otherwise indicate that the hip has essentially begun to lower the foot, as described above, the immediate response of the prosthesis is to essentially switch into an early stance phase. That is, stiffen the knee joint to support the weight of the user and increase damping at the ankle joint to facilitate stable contact and conformation between the foot and ground. Additionally, as is the case in the lowering type stumble response in healthy individuals, the subsequent stride (with the lowered limb) can be configured to exhibit an exaggerated amount of knee flexion and ankle dorsiflexion during the swing, in order to clear the object that presumably caused the stumble event. The respective exaggerated motions in the two joints of the prosthesis can be generated in the subsequent swing phase by altering the appropriate equilibrium points in the coordination level controllers. This is illustrated in FIG. 8.

Figure 8:
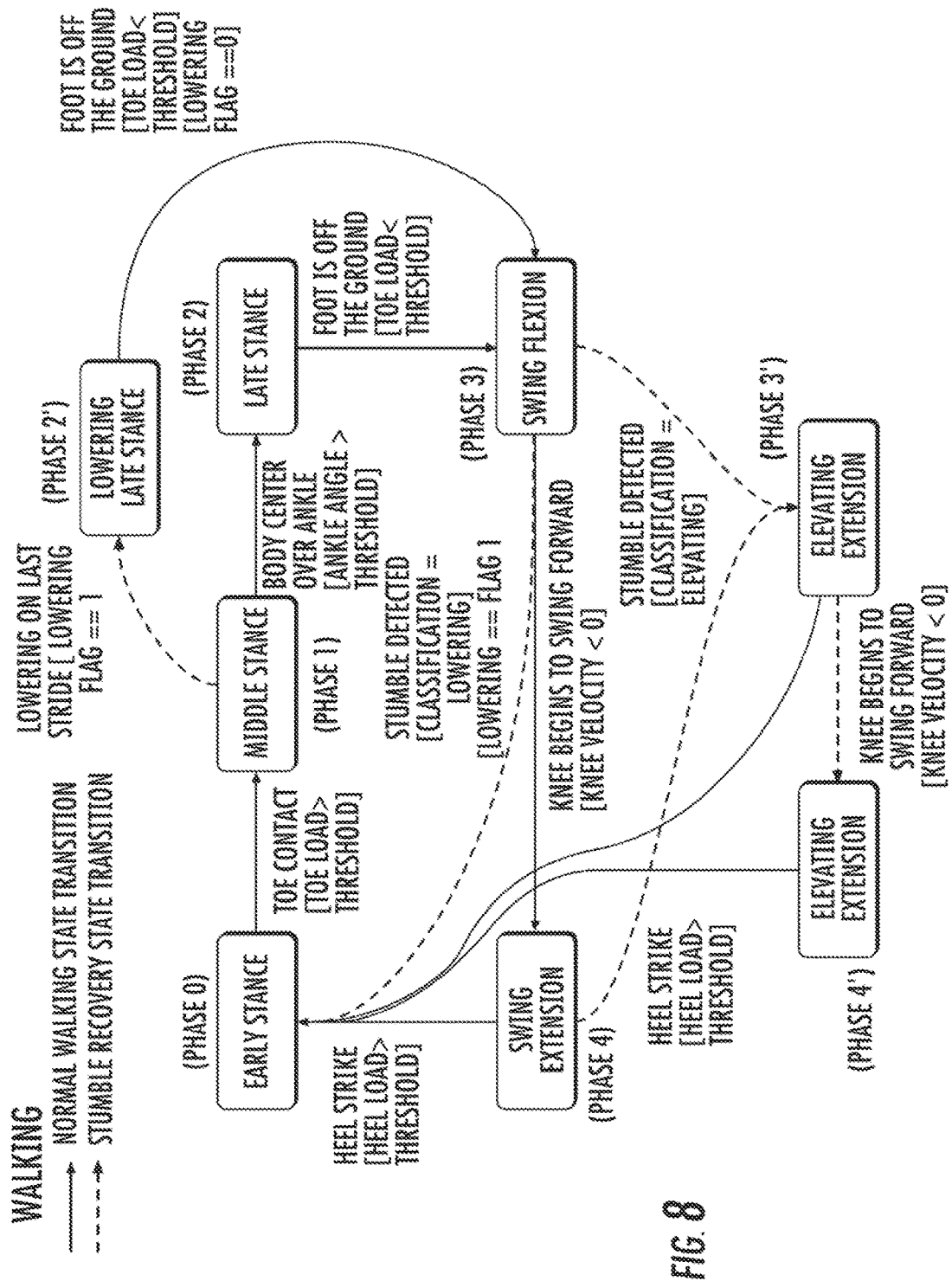
FIG. 8 shows exemplary switching rules between internal phases for walking for the walking portion of the exemplary control system of FIG. 4 adapted to include a stumble response in accordance with an embodiment of the invention.

FIG. 8 shows exemplary switching rules between internal phases for walking for the walking portion of the exemplary control system of FIG. 4 adapted to include a stumble response in accordance with an embodiment of the invention. During walking the switching rules cause the prosthesis to switch between phases. During a stumble event, different parameters, different switching between phases, or additional state switching can be provided to reduce the likelihood of falls.

As described above, a typical human response to a stumble generally results in one of an elevating or lowering response. In the case of the lowering response, the intent is to stabilize oneself by bringing one's foot down to the ground as soon as possible and stiffen the knee in order to bear weight on the lowered leg. This functionality can be provided in the walking controller of FIG. 4 without significant changes and without the need for a separate, dedicated stumble recovery controller. That is, without the need to detect the occurrence of a lowering stumble event. In the particular, the walking controller can be configured to switch the powered prosthetic leg into an early stance phase when premature ground contact of the foot is detected, i.e., transition to Phase 0. Thus, the powered prosthetic leg is adjusted in accordance with the knee impedance parameters characteristic of early stance phase (i.e., the knee will stiffen to support the weight of the user, and the ankle will exhibit damping to facilitate stable ground contact).

In some configurations, the walking controller can also be configured to clear the obstacle causing the stumble during a subsequent swing of the prosthetic leg. That is, if a prior stumble associated with a lowering strategy was detected (via premature ground contact or measurement of acceleration), the impedance parameters for the leg can be adjusted, as shown in FIG. 8. During the subsequent swing, the controller can provide an exaggerated version of the normal swing in order to clear the obstacle. This can be implemented in a control system, as follows.

When a stumble event occurs at any point during the swing (i.e., during the transition from Phase 3 to Phase 4) and a lowering strategy is utilized, the controller, as described above, can immediately transition to the early stance (Phase 0). However, in order to provide the exaggerated swing, a flag or other value in memory (e.g., "Lowering Flag" in FIG. 8) can be stored to indicate the past occurrence of such a stumble. This flag thus causes FIG. 8 to transitions from the middle stance (Phase 1) a lowering late stance (Phase 2') instead of the normal late stance. At Phase 2', the lower limb device has impedance parameters that provide an exaggerated push-off, which in turn generates an exaggerated swing for obstacle clearance. Because the push-off of Phase 2' provides more energy to the system, the impedance parameters of the swing phases do not need to be altered in order to achieve the exaggerated swing. Thereafter, the flag is cleared or reset and the control system transitions back to the normal state progression (i.e., Phase 3). Thus during a subsequent swing, the configuration provided at the lowering state stance allows the lower limb device to clear the obstacle.

In the case that an elevating strategy is identified, the intent is to try to immediately overcome the obstacle and complete the swing of the prosthetic leg. To provide such functionality, a separate stumble recovery controller can be used in combination with the walking controller. That is, if a stumble is detected and is classified as elevating, the walking controller can pass control to the stumble recovery controller to provide an elevating response, as shown in FIG. 8. That is, the stumble recovery controller is employed to first flex the knee and dorsiflex the ankle joints (to clear the object precipitating the stumble) at Phase 3', followed by extension of the knee joint (to place the foot in front of the subject) in order to arrest the forward angular momentum imparted by the stumble at Phase 4'. Such a response is essentially an exaggerated version of the normal swing phase controller and is thus easily accommodated within the existing finite-state impedance control framework of FIG. 4. That is, the finite state structure shown in FIG. 4 can be modified slightly as shown in FIG. 8, such that upon detection of the elevating stumble an "alternate swing Phase" loop (via phases 3' and 4') is followed until ground contact (premature or otherwise) is detected. Thus, the difference between the two loops is essentially the impedance parameters (i.e., joint stiffness, damping, and equilibrium point or trajectory).

Note that the above structure can similarly be incorporated into a transtibial prosthesis with a powered ankle joint. Specifically, in the case of an elevating response, the ankle joint would provide active dorsiflexion, in order to help the foot clear the obstacle. In the case of a lowering response, the ankle would initially provide appropriate stance behavior and then exaggerated push-off to help clear the obstacle during the subsequent stride.

Although the various embodiments of the invention are mainly described in terms of a stumble occurring with a prosthesis, the invention is not limited in this regard. Rather, the various embodiments are also operable to provide stumble recovery when a user stumbles with the sound leg. However, such stumble recovery is provided by the normal operation of the walking controller. That is, in the case of sound leg lowering, the forward trajectory of the center of mass (COM) of the user will trigger (an early) swing phase for the prosthesis. Thus, the foot is lifted off the ground, causing the foot load sensors to trigger the transition from Phase 2 to Phase 3. Should the foot contact the ground (i.e., prior to Phase 4), prematurely, the lowering response described above can be triggered and the leg can transition to an early stance (Phase 0), as previously described. In the case of sound leg elevating, this results in a continued load being imposed on the prosthesis. Thus, since the transition from a stance phase to a swing phase of the leg (Phase 2 to Phase 3) does not occur until such a load is removed, the walking controller will maintain the stance phase, and thus a stiffened knee joint.

In addition to stumble recovery, a powered prosthesis can also be used for ground adaptation. Passive prostheses generally cannot adapt to uneven ground, and therefore often do not provide stabilizing assistance while standing, and sometimes provide destabilizing effects, as described below with respect to FIGS. 9A-9E.

FIGS. 9A-9C depict a transfemoral amputee subject, wearing a state-of-the-art passive prosthesis (i.e., an Otto Bock C-leg with a Freedom Renegade ankle/foot), including a knee joint, for various slopes. Consider first the case of a transfemoral amputee on level ground, as represented in FIG. 9A. In this case, the (prosthetic) foot is flat on the ground, the ankle is stiff (by design), and the knee is "locked" against hyperextension stops, and thus the prosthesis possesses the structural ability to transmit the stabilizing moment from the ground to the COM. In this circumstance, the amputee can put weight on the prosthesis, and will receive stabilizing assistance from it. Consider now the case shown in FIG. 9B, in which the amputee is standing on a downward slope. In this case, the center of pressure (COP) lies within the foot, which lies flat on the ground, and thus a stabilizing moment (in the form of the ankle stiffness) can be transmitted between the ground and the shank. The body COM, however, lies posterior to the knee joint, and as such prosthetic knees are typically not capable of transmitting the stabilizing (stiffness) moment from the shank to the thigh (since doing so would create complications at toe-off during walking). Thus, in the case of standing on a downward slope, the prosthesis will offer little stabilizing assistance to the user (note that a small degree of assistance is afforded dynamically through the damping characteristics of the knee).

The result is similar when standing on an upward slope, as illustrated in FIG. 9C, although for different reasons. Specifically, in this case, the knee is hyperextended and able to transmit a stabilizing moment from the shank to the thigh, but (due to the inability of the ankle to realign its equilibrium point), the foot is not flat on the ground, and thus a moment cannot be transmitted between the ground and shank (and thus cannot be transmitted between the mound and COM). As such, the user derives little or no balance assistance from the prosthesis when standing on an upward slope. Note that the foot of the prosthesis could be forced to be flat on the ground, but (since the equilibrium point of the ankle stiffness is essentially at zero) doing so will generate a destabilizing moment, thus exacerbating imbalance.

To overcome such standing stability issues, enabling stabilizing assistance from the prosthesis on ascending and descending slopes is a matter of 1) identifying the ground slope and appropriately shifting the equilibrium point of the ankle torque controller (i.e., $\theta_i$ in the control equation $\tau_i = k_i(\theta - \theta_i) + b_i\dot{\theta}$, and 2) ensuring that the knee remains sufficiently stiff when load is applied to the limb. Note that the latter is already a property of the middle-level finite-state impedance-based standing controller shown in FIG. 4. Thus, enhanced stability for upslope and downslope standing is enabled in the powered prosthesis by estimating ground slope and adapting the ankle equilibrium point and stiffness appropriately.

In the various embodiments of the invention, slope estimation is obtained as follows. First, when the prosthesis is in a non-weight-bearing state (such as during swing of the prosthesis or a sitting activity), the ankle joint is characterized by a low rotational stiffness. Specifically, the rotational stiffness is sufficiently high to prevent foot drop, but low enough that subsequently placing a significant portion of the body weight (e.g., >10%) on the prosthesis will cause the ankle to deflect such that the plantar side or surface of foot conforms to the slope of the ground (i.e., flat on the ground).

Once the foot is flat on the ground, as determined by the heel and ball of foot load sensors, a 3-axis accelerometer can be used to determine the ground slope. Specifically, assuming the ground is an inertial reference frame, the only component of acceleration once the foot is flat on the ground (assuming no slip) is the gravitational acceleration, and as such, the relative values of the respective components measured by the 3-axis accelerometer can be used to determine the orientation of the gravitational vector relative to the foot, and thus the ground slope is known. It is worth noting that the amount of additional sensor hardware required for the ground slope estimation can be minimal with respect to the total mass and power requirements of the prosthesis.

Exemplary results of real-time ground slope estimation are shown in FIG. 10. FIG. 10 shows real-time ground slope estimation obtained from a transfemoral amputee standing on various ramps of various slopes (+5, +10, −10, and −5). To generate the data shown in FIG. 10, the amputee stood initially on level ground and moved from one ramp to the next, while standing on each ramp for approximately 10 seconds. For the data shown in FIG. 10, both the sensor input and the estimator output are filtered with first-order 20 Hz low-pass filters. As shown in FIG. 10, good agreement was obtained between actual and estimated slope.

In some embodiments of the invention, the rotational stiffness of the knee can also be adjusted. First, when the prosthesis is in a non-weight-bearing state (such as during swing of the prosthesis or a sitting activity), the knee joint is also characterized by a lower rotational stiffness to allow the knee joint to deflect during a swing phase. Thereafter, once the foot makes initial contact with the ground, a high rotational stiffness can be provided as the ankle joint deflects and the prosthesis begins to bear the weight of the amputee.

Figure 11:
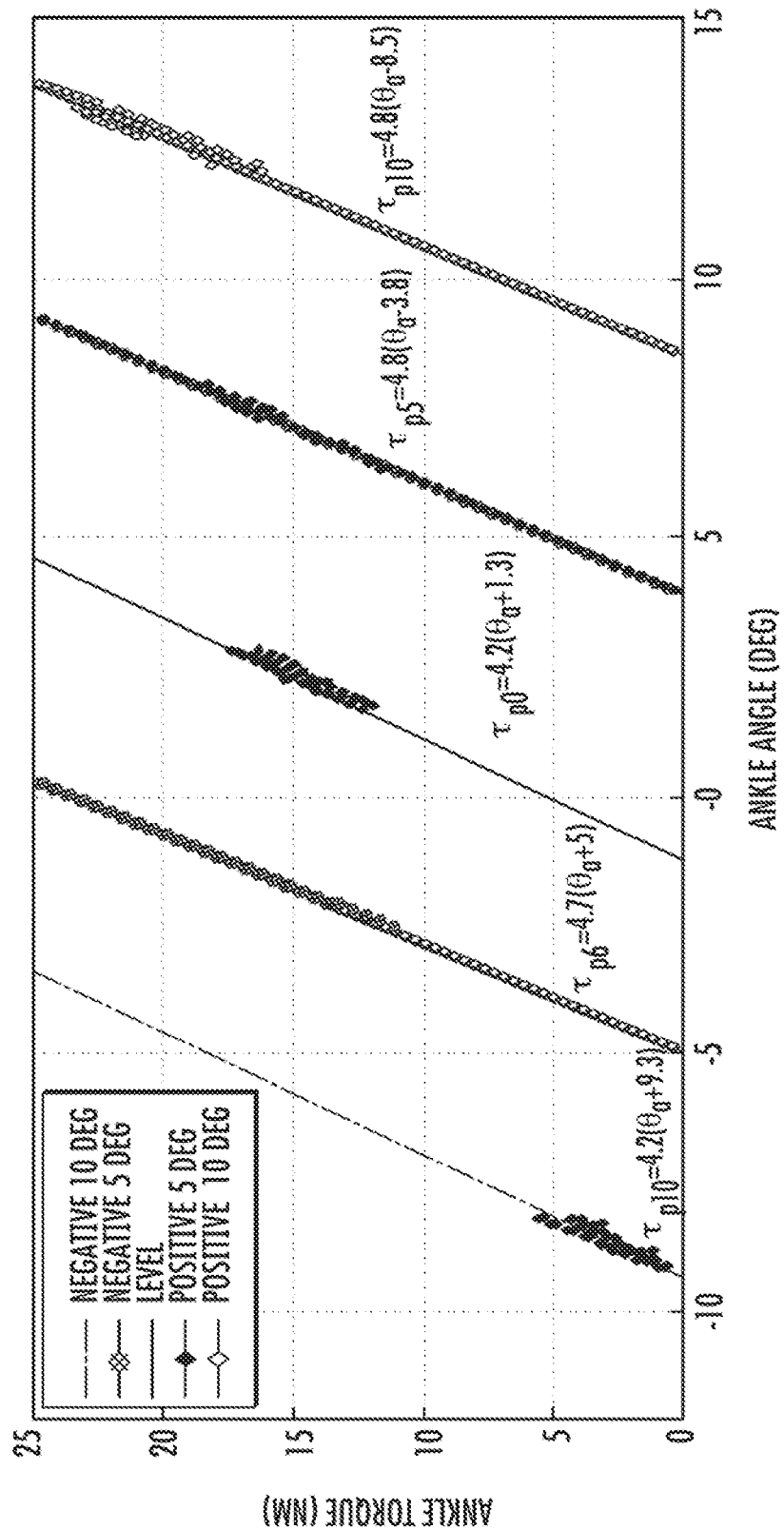
FIG. 11 shows the ankle torque versus ankle angle during quiet standing for each of the ground slopes in FIG. 10 for a powered prosthesis configured in accordance with an embodiment of the invention.
Figures 12A, 12B, 12C, 12D, 12E:
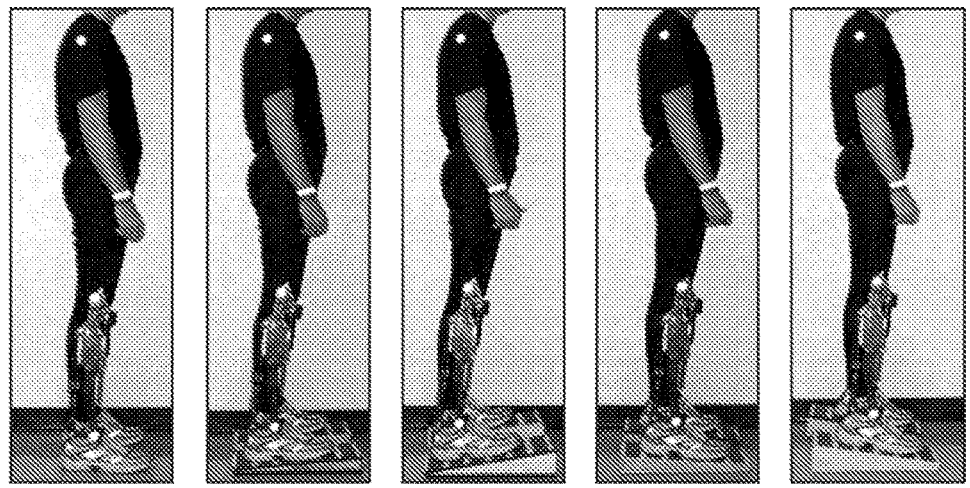
FIGS. 12A-12E depicts a transfemoral amputee subject, wearing a powered prosthesis in accordance with an embodiment of the invention for each of the ground slopes in FIG. 10.

FIG. 11 shows an X-Y plot of measured ankle joint torque versus angle for varying ground slopes, showing the ability of the ankle to adapt to and provide stabilizing assistance in each ground slope scenario in FIG. 10. Specifically, FIG. 11 shows the ankle torque versus ankle angle during quiet standing for each of the ground slopes, along with a least-squares fit to the data corresponding to each ground slope, demonstrating the ability of the powered prosthesis to adapt its behavior to each, thus enabling stabilizing assistance across all ground slopes. A passive prosthesis would in all ground slope scenarios maintain the behavior exhibited in the center set of data, which (assuming the foot remained flat on the ground) would at torsional equilibrium locate the center of pressure behind the user's feet on the downslope, and in front of the user on the upslope (and thus would be a destabilizing influence in all cases). As further demonstrated by the data in FIG. 11, the powered prosthesis appropriately shifts its ankle equilibrium such that the energetic minimum of the (ankle) potential field acts to maintain the body COM over the feet, and thus provides stabilizing assistance to the user, as shown in FIGS. 12A-12B. FIGS. 12A-12E depict a transfemoral amputee subject, wearing a powered prosthesis in accordance with an embodiment of the invention for each of the ground slopes in FIG. 10.

The configuration described above additionally results in improved load bearing over conventional passive prostheses. The distribution of load bearing for all ground slope scenarios for both prostheses (i.e., the scenarios depicted by FIGS. 12A-12E) is shown in FIG. 13.

Figure 13:
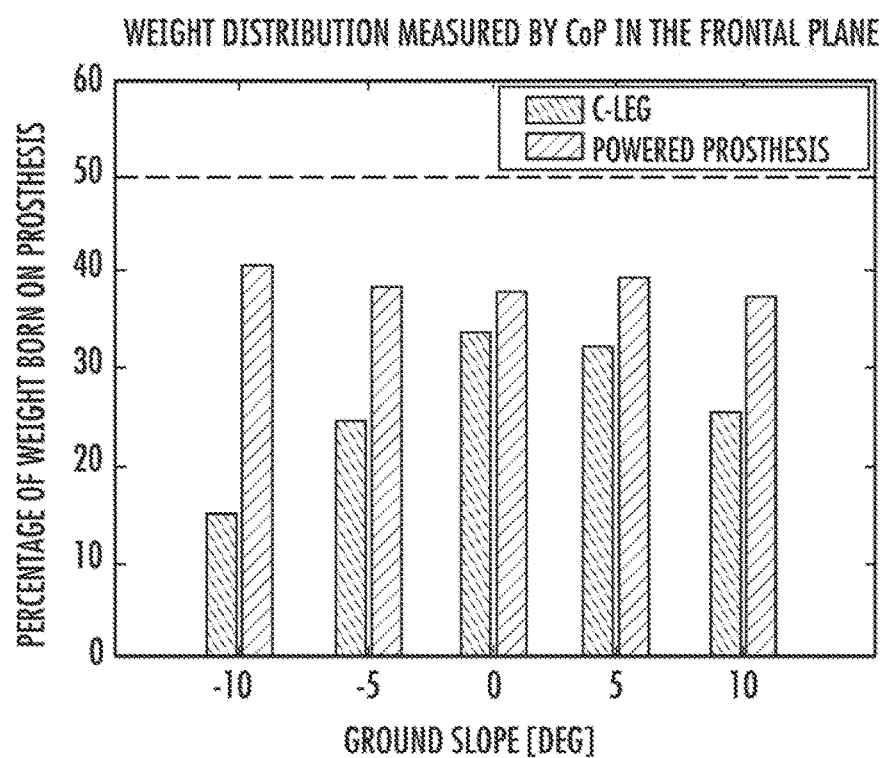
FIG. 13 is a plot of the ratio of prosthetic/sound leg weight bearing for a passive prosthesis, as described above, and a powered prosthesis configured in accordance with an embodiment of the invention for five ground slopes in FIG. 10.

FIG. 13 is a plot of the ratio of prosthetic/sound leg weight bearing for a passive prosthesis, as described above, and a powered prosthesis configured in accordance with an embodiment of the invention for five ground slopes. As shown in FIG. 13, the powered prosthesis maintains a roughly constant ratio near 40% (i.e., 60% of load on sound side, 40% on prosthesis), while the passive prosthesis varies between approximately 15% (on the 10 degree downslope) and 35% (on level ground). As indicated by the data in FIG. 13, the powered prosthesis is able to sustain a significantly increased load, and thus is better able to provide stabilizing assistance in when standing, particularly in the frontal plane.

In some embodiments of the invention, for the frontal plane uneven terrain circumstances, the powered prosthesis can be configured for detecting ground contact (using a similar approach to that described for ground slope estimation), and "stiffening" the knee and ankle joints about the respective joint angles in the ground contact configuration (in a similar manner to the ankle adjustment previously described), thus enabling load improved transmission through the prosthesis, and thus providing for stabilizing assistance in both the sagittal and the frontal planes.

Although the ground slope adaptation techniques described herein effectively provide for improved transmission of forces and moments between the ground and body COM during standing, these techniques can also be used to similarly provide for improved transmission force and moment during the stance phase of gait. As such, the previously described ground slope estimation approach can also be used to adjust the impedance parameters of the walking controller to accommodate uneven terrain during walking. Thus, the stability of both standing and walking (especially in cases of uneven terrain) can be provided in the various embodiments of the invention, leading to a decrease the incidence of stumbling in transfemoral amputee gait.

While various embodiments of the invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the invention should not be limited by any of the above described embodiments. Rather, the scope of the invention should be defined in accordance with the following claims and their equivalents.

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the at to which this invention belongs. It is further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method of controlling a prosthetic lower limb device comprising a powered knee joint, the method comprising:
   detecting a stumble event based on one or more sensor signals associated with at least an overall motion of the prosthetic lower limb device;
   classifying a likely response strategy for the stumble event as a lowering strategy or an elevating strategy based on the sensor signals after the stumble event, the classifying comprising:
      estimating at least one measure of a motion of a residual limb associated with the prosthetic lower limb device based on the sensor signals,
      comparing the at least one measure to a threshold amount, and
      choosing one of the lowering strategy or the elevating strategy as the likely response strategy based on the comparing; and
   configuring the powered knee joint of the prosthetic lower limb device to operate according to one of a lowering response corresponding to the lowering strategy or an elevating response corresponding to the elevating strategy based on the classifying,
   wherein the lowering response comprises extension of the prosthetic lower limb device relative to the powered knee joint, and wherein the elevating response comprises an initial flexion of the prosthetic lower limb device relative to the powered knee joint and a subsequent extension of the prosthetic lower limb device relative to the powered knee joint.

2. The method of claim 1, wherein the stumble event is detected when at least one the sensor signal in the first portion meets a pre-defined criteria.

3. The method of claim 1, wherein the estimating of the at least one measure of the motion of the residual limb comprises estimating an acceleration of the residual limb.

4. The method of claim 1, wherein the elevating strategy is chosen if the at least one measure of the motion of the residual limb is less than the threshold amount, and wherein the lowering strategy is chosen if the at least one measure of the motion is greater than or equal to the threshold amount.

5. The method of claim 1, wherein the lower limb device comprises a foot portion comprising one or more load sensors, and wherein the lowering response is selected when one or more signals from the load sensors meets a predefined criteria.

6. The method of claim 1, wherein the step of configuring the prosthetic lower limb device to operate according to the lowering response further comprises configuring the powered knee joint to stiffen the powered knee joint after the extension of the prosthetic lower limb device relative to the powered knee joint and to exaggerate flexion for the prosthetic lower limb device during a subsequent swing phase.

7. The method of claim 6, wherein the lowered limb device further comprises a foot portion and a powered ankle joint, and wherein the step of configuring the lower limb device to operate according to the lowering response further comprises:
   reducing an impedance of the powered ankle joint until a plantar surface of the foot portion conforms to a walking surface; and
   increasing the impedance of the ankle joint after the plantar surface of the foot portion conforms to the walking surface.

8. The method of claim 1, wherein the step of configuring the prosthetic lower limb device to operate according to the elevating response further comprises:
   detecting an end of a swing of the residual limb and the prosthetic lower limb device based on the sensor signals; and
   responsive to detection of the end of the swing, configuring the powered knee joint to support the weight of a user of the prosthetic lower limb device.

9. The method of claim 8, wherein the powered joint further comprises a powered ankle joint, and wherein the elevating response further comprises dorsiflexion of the ankle joint.

10. The method of claim 1 wherein the at least one measure is based on the sensor signals corresponding to a time window following the stumble event.

* * * * *

UNITED STATES PATENT AND TRADEMARK OFFICE
CERTIFICATE OF CORRECTION

PATENT NO. : 9,750,620 B2
APPLICATION NO. : 13/508175
DATED : September 5, 2017
INVENTOR(S) : Goldfarb et al.

Page 1 of 1

It is certified that error appears in the above-identified patent and that said Letters Patent is hereby corrected as shown below:

In the Specification

In Column 1, at Line 15, after the section entitled CROSS-REFERENCE TO RELATED APPLICATIONS, insert the following heading and paragraph:
--GOVERNMENT SUPPORT
This invention was made with Government support under grant number EB005684 awarded by the National Institutes of Health. The Government has certain rights in the invention.--

Signed and Sealed this
Twenty-sixth Day of November, 2019

Andrei Iancu
*Director of the United States Patent and Trademark Office*